(12) United States Patent
Winter

(10) Patent No.: US 7,892,270 B2
(45) Date of Patent: Feb. 22, 2011

(54) TEMPERATURE MANAGEMENT SYSTEM AND METHOD FOR BURN PATIENTS

(75) Inventor: Suzanne Winter, Grass Valley, CA (US)

(73) Assignee: Zoll Circulation Inc., Sunnyvale, CA (US)

( * ) Notice: Subject to any disclaimer, the term of this patent is extended or adjusted under 35 U.S.C. 154(b) by 1128 days.

(21) Appl. No.: 11/602,738

(22) Filed: Nov. 21, 2006

(65) Prior Publication Data

US 2008/0119788 A1   May 22, 2008

(51) Int. Cl.
*A61F 7/12*   (2006.01)
(52) U.S. Cl. .................. 607/105; 607/104; 607/106
(58) Field of Classification Search ............ 607/96, 607/104–107
See application file for complete search history.

(56) References Cited

U.S. PATENT DOCUMENTS

| | | | |
|---|---|---|---|
| 5,207,640 A | 5/1993 | Hattler | 604/28 |
| 5,230,862 A | 7/1993 | Berry et al. | 422/48 |
| 5,271,743 A | 12/1993 | Hattler | 604/26 |
| 5,450,516 A | 9/1995 | Pasquali et al. | 385/115 |
| 5,470,659 A | 11/1995 | Baumgart et al. | 428/398 |
| RE35,330 E * | 9/1996 | Malone et al. | 606/28 |
| 5,725,949 A | 3/1998 | Pasquali et al. | 428/398 |
| 5,735,809 A | 4/1998 | Gorsuch | 428/364 |
| 5,755,690 A | 5/1998 | Saab | 604/96 |
| 5,837,003 A | 11/1998 | Ginsburg | 607/106 |
| 5,876,667 A | 3/1999 | Gremel et al. | 604/4 |
| 5,879,329 A | 3/1999 | Ginsburg | 604/93 |
| 5,989,238 A | 11/1999 | Ginsburg | 604/93 |
| 6,004,289 A | 12/1999 | Saab | 604/96 |
| 6,019,783 A | 2/2000 | Philips | 607/105 |
| 6,042,559 A | 3/2000 | Dobak | 604/7 |
| 6,096,068 A | 8/2000 | Dobak | 607/105 |
| 6,110,168 A | 8/2000 | Ginsburg | 606/27 |
| 6,126,684 A | 10/2000 | Gobin | 607/113 |
| 6,146,411 A | 11/2000 | Noda | 607/105 |
| 6,149,670 A | 11/2000 | Worthen | 607/3 |
| 6,149,673 A | 11/2000 | Ginsburg | 607/96 |
| 6,149,676 A | 11/2000 | Ginsburg | 607/106 |
| 6,149,677 A | 11/2000 | Dobak | 607/106 |
| 6,165,207 A | 12/2000 | Balding | 607/105 |
| 6,224,624 B1 | 5/2001 | Lasheras | 607/105 |
| 6,231,594 B1 | 5/2001 | Dae | 607/96 |
| 6,231,595 B1 | 5/2001 | Dobak | 607/106 |
| 6,235,048 B1 | 5/2001 | Dobak | 607/104 |
| 6,238,428 B1 | 5/2001 | Werneth | 607/105 |
| 6,245,095 B1 | 6/2001 | Dobak | 607/105 |
| 6,251,129 B1 | 6/2001 | Dobak | 607/105 |
| 6,251,130 B1 | 6/2001 | Dobak | 607/105 |
| 6,254,626 B1 | 7/2001 | Dobak | 607/105 |
| 6,264,679 B1 | 7/2001 | Keller | 607/105 |
| 6,287,326 B1 | 9/2001 | Pecor | 607/105 |
| 6,290,717 B1 | 9/2001 | Philips | 607/113 |
| 6,299,599 B1 | 10/2001 | Pham | 604/113 |
| 6,306,161 B1 | 10/2001 | Ginsburg | 607/106 |
| 6,312,452 B1 | 11/2001 | Dobak | 607/105 |

(Continued)

OTHER PUBLICATIONS

U.S. Appl. No. 60/272,442, Worthen et al.

*Primary Examiner*—Roy D Gibson
(74) *Attorney, Agent, or Firm*—John L. Rogitz

(57) ABSTRACT

Intravascular closed loop heat exchange catheters are used to manage temperature in burn patients.

11 Claims, 2 Drawing Sheets

U.S. PATENT DOCUMENTS

| | | | |
|---|---|---|---|
| 6,325,818 B1 | 12/2001 | Werneth | 607/105 |
| 6,338,727 B1 | 1/2002 | Noda | 604/113 |
| 6,364,899 B1 | 4/2002 | Dobak | 607/113 |
| 6,368,304 B1 | 4/2002 | Aliberto | 604/113 |
| 6,379,378 B1 | 4/2002 | Werneth | 607/96 |
| 6,383,210 B1 | 5/2002 | Magers et al. | 607/105 |
| 6,393,320 B2 | 5/2002 | Lasersohn | 607/3 |
| 6,405,080 B1 | 6/2002 | Lasersohn | 607/3 |
| 6,409,747 B1 | 6/2002 | Gobin | 607/113 |
| 6,416,533 B1 | 7/2002 | Gobin | 607/113 |
| 6,419,643 B1 | 7/2002 | Shimada | 600/323 |
| 6,428,563 B1 | 8/2002 | Keller | 607/105 |
| 6,432,124 B1 | 8/2002 | Worthen | 607/105 |
| 6,436,130 B1 | 8/2002 | Philips | 607/105 |
| 6,436,131 B1 | 8/2002 | Ginsburg | 607/106 |
| 6,440,158 B1 | 8/2002 | Saab | 604/105 |
| 6,447,474 B1 | 9/2002 | Balding | 604/66 |
| 6,450,987 B1 | 9/2002 | Kramer | 604/523 |
| 6,450,990 B1 | 9/2002 | Walker | 604/113 |
| 6,451,045 B1 | 9/2002 | Walker | 607/105 |
| 6,454,792 B1 | 9/2002 | Noda | 607/105 |
| 6,454,793 B1 | 9/2002 | Evans | 607/105 |
| 6,458,150 B1 | 10/2002 | Evans | 607/105 |
| 6,460,544 B1 | 10/2002 | Worthen | 607/105 |
| 6,464,716 B1 | 10/2002 | Dobak | 607/105 |
| 6,468,296 B1 | 10/2002 | Dobak | 607/105 |
| 6,471,717 B1 | 10/2002 | Dobak | 607/105 |
| 6,475,231 B2 | 11/2002 | Dobak | 607/105 |
| 6,478,811 B1 | 11/2002 | Dobak | 607/105 |
| 6,478,812 B2 | 11/2002 | Dobak | 607/105 |
| 6,482,226 B1 | 11/2002 | Dobak | 607/104 |
| 6,491,039 B1 | 12/2002 | Dobak | 128/898 |
| 6,491,716 B2 | 12/2002 | Dobak | 607/105 |
| 6,494,903 B2 | 12/2002 | Pecor | 607/105 |
| 6,497,721 B2 | 12/2002 | Ginsburg | 607/106 |
| 6,516,224 B2 | 2/2003 | Lasersohn | 607/3 |
| 6,520,933 B1 | 2/2003 | Evans | 604/103.07 |
| 6,527,798 B2 | 3/2003 | Ginsburg | 607/106 |
| 6,529,775 B2 | 3/2003 | Whitebook | 607/100 |
| 6,530,946 B1 | 3/2003 | Noda | 607/113 |
| 6,533,804 B2 | 3/2003 | Dobak | 607/105 |
| 6,540,771 B2 | 4/2003 | Dobak | 607/105 |
| 6,544,282 B1 | 4/2003 | Dae | 607/105 |
| 6,551,349 B2 | 4/2003 | Lasheras | 607/105 |
| 6,554,797 B1 | 4/2003 | Worthen | 604/113 |
| 6,558,412 B2 | 5/2003 | Dobak | 607/105 |
| 6,572,538 B2 | 6/2003 | Takase | 600/140 |
| 6,572,638 B1 | 6/2003 | Dae et al. | 607/96 |
| 6,572,640 B1 | 6/2003 | Balding | 607/105 |
| 6,576,001 B2 | 6/2003 | Werneth | 607/96 |
| 6,576,002 B2 | 6/2003 | Dobak | 607/105 |
| 6,581,403 B2 | 6/2003 | Whitebook | 62/434 |
| 6,582,398 B1 | 6/2003 | Worthen | 604/113 |
| 6,582,455 B1 | 6/2003 | Dobak | 607/105 |
| 6,582,457 B2 | 6/2003 | Dae | 607/113 |
| 6,585,692 B1 | 7/2003 | Worthen | 604/113 |
| 6,585,752 B2 | 7/2003 | Dobak | 607/105 |
| 6,589,271 B1 | 7/2003 | Tzeng | 607/113 |
| 6,595,967 B2 | 7/2003 | Kramer | 604/523 |
| 6,599,312 B2 | 7/2003 | Dobak | 607/105 |
| 6,602,243 B2 | 8/2003 | Noda | 604/544 |
| 6,602,276 B2 | 8/2003 | Dobak | 607/105 |
| 6,607,517 B1 | 8/2003 | Dae | 604/31 |
| 6,610,083 B2 | 8/2003 | Keller | 607/105 |
| 6,620,130 B1 | 9/2003 | Ginsburg | 604/113 |
| 6,620,131 B2 | 9/2003 | Pham | 604/113 |
| 6,620,188 B1 | 9/2003 | Ginsburg | 607/106 |
| 6,620,189 B1 | 9/2003 | MacHold | 607/106 |
| 6,623,516 B2 | 9/2003 | Saab | 607/105 |
| 6,635,076 B2 | 10/2003 | Ginsburg | 607/106 |
| 6,641,602 B2 | 11/2003 | Balding | 607/105 |
| 6,641,603 B2 | 11/2003 | Walker | 607/105 |
| 6,645,234 B2 | 11/2003 | Evans | 607/113 |
| 6,648,906 B2 | 11/2003 | Lasheras | 607/105 |
| 6,648,908 B2 | 11/2003 | Dobak | 607/105 |
| 6,652,565 B1 | 11/2003 | Shimada | 607/113 |
| 6,656,209 B1 | 12/2003 | Ginsburg | 607/106 |
| 6,660,028 B2 | 12/2003 | Magers | 607/105 |
| 6,673,098 B1 | 1/2004 | MacHold | 607/106 |
| 6,676,688 B2 | 1/2004 | Dobak | 607/105 |
| 6,676,689 B2 | 1/2004 | Dobak | 607/105 |
| 6,676,690 B2 | 1/2004 | Werneth | 607/105 |
| 6,679,906 B2 | 1/2004 | Hammack | 607/105 |
| 6,679,907 B2 | 1/2004 | Dobak | 607/105 |
| 6,682,551 B1 | 1/2004 | Worthen | 607/105 |
| 6,685,732 B2 | 2/2004 | Kramer | 607/106 |
| 6,685,733 B1 | 2/2004 | Dae | 607/105 |
| 6,692,488 B2 | 2/2004 | Dobak | 606/21 |
| 6,692,519 B1 | 2/2004 | Hayes | 607/105 |
| 6,695,873 B2 | 2/2004 | Dobak | 607/105 |
| 6,695,874 B2 | 2/2004 | Machold | 607/106 |
| 6,699,268 B2 | 3/2004 | Kordis | 607/113 |
| 6,702,783 B1 | 3/2004 | Dae | 604/113 |
| 6,702,839 B1 | 3/2004 | Dae | 607/96 |
| 6,702,840 B2 | 3/2004 | Keller | 607/105 |
| 6,702,841 B2 | 3/2004 | Nest | 607/105 |
| 6,702,842 B2 | 3/2004 | Dobak | 607/105 |
| 6,706,060 B2 | 3/2004 | Tzeng | 607/105 |
| 6,709,448 B2 | 3/2004 | Walker | 607/105 |
| 6,716,188 B2 | 4/2004 | Noda | 604/6.13 |
| 6,716,236 B1 | 4/2004 | Tzeng | 607/113 |
| 6,719,723 B2 | 4/2004 | Werneth | 604/113 |
| 6,719,724 B1 | 4/2004 | Walker | 604/113 |
| 6,719,779 B2 | 4/2004 | Daoud | 607/105 |
| 6,726,653 B2 | 4/2004 | Noda | 604/113 |
| 6,726,708 B2 | 4/2004 | Lasheras | 607/105 |
| 6,726,710 B2 | 4/2004 | Worthen | 607/105 |
| 6,733,517 B1 | 5/2004 | Collins | 607/105 |
| 6,740,109 B2 | 5/2004 | Dobak | 607/105 |
| 6,749,585 B2 | 6/2004 | Aliberto | 604/113 |
| 6,749,625 B2 | 6/2004 | Pompa | 607/105 |
| 6,752,786 B2 | 6/2004 | Callister | 604/113 |
| 6,755,850 B2 | 6/2004 | Dobak | 607/104 |
| 6,755,851 B2 | 6/2004 | Noda | 607/113 |
| 2001/0007951 A1 | 7/2001 | Dobak, III | 607/106 |
| 2001/0016764 A1 | 8/2001 | Dobak, III | 607/105 |
| 2001/0041923 A1 | 11/2001 | Dobak, III | 607/105 |
| 2002/0007203 A1 | 1/2002 | Gilmartin et al. | 607/105 |
| 2002/0016621 A1 | 2/2002 | Werneth et al. | 607/96 |
| 2002/0068964 A1 | 6/2002 | Dobak, III | 607/113 |
| 2002/0077680 A1 | 6/2002 | Noda | 600/549 |
| 2002/0091429 A1 | 7/2002 | Dobak, III et al. | 607/105 |
| 2002/0111616 A1 | 8/2002 | Dea et al. | 606/27 |
| 2002/0151946 A1 | 10/2002 | Dobak, III | 607/105 |
| 2002/0177804 A1 | 11/2002 | Saab | 607/105 |
| 2002/0183692 A1 | 12/2002 | Callister | 604/113 |
| 2002/0193738 A1 | 12/2002 | Adzich et al. | 604/113 |
| 2002/0193853 A1 | 12/2002 | Worthen et al. | 607/3 |
| 2002/0193854 A1 | 12/2002 | Dobak, III et al. | 607/105 |
| 2003/0078641 A1 | 4/2003 | Dobak, III | 607/105 |
| 2003/0114835 A1 | 6/2003 | Noda | 604/544 |
| 2003/0144714 A1 | 7/2003 | Dobak, III et al. | 607/104 |
| 2003/0187489 A1 | 10/2003 | Dobak, III et al. | 607/105 |
| 2003/0195465 A1 | 10/2003 | Worthen | 604/113 |
| 2003/0195466 A1 | 10/2003 | Pham | 604/113 |
| 2003/0195597 A1 | 10/2003 | Keller et al. | 607/105 |
| 2003/0216799 A1 | 11/2003 | Worthen | 606/27 |
| 2004/0044388 A1 | 3/2004 | Pham et al. | 607/105 |
| 2004/0087934 A1 | 5/2004 | Dobak, III et al. | |
| 2004/0102825 A1 | 5/2004 | Daoud | |
| 2004/0102826 A1 | 5/2004 | Lasheras | |
| 2004/0102827 A1 | 5/2004 | Werneth | |
| 2004/0106969 A1 | 6/2004 | Dobak, III et al. | |
| 2004/0116987 A1 | 6/2004 | Magers et al. | |

| | | | | | |
|---|---|---|---|---|---|
| 2004/0116988 A1 | 6/2004 | Hammack et al. | 2005/0043579 A1 | 2/2005 | Dae et al. |
| 2004/0127851 A1 | 7/2004 | Noda et al. .............. 604/503 | | | |
| 2005/0038079 A1 | 2/2005 | Cooke et al. | * cited by examiner | | |

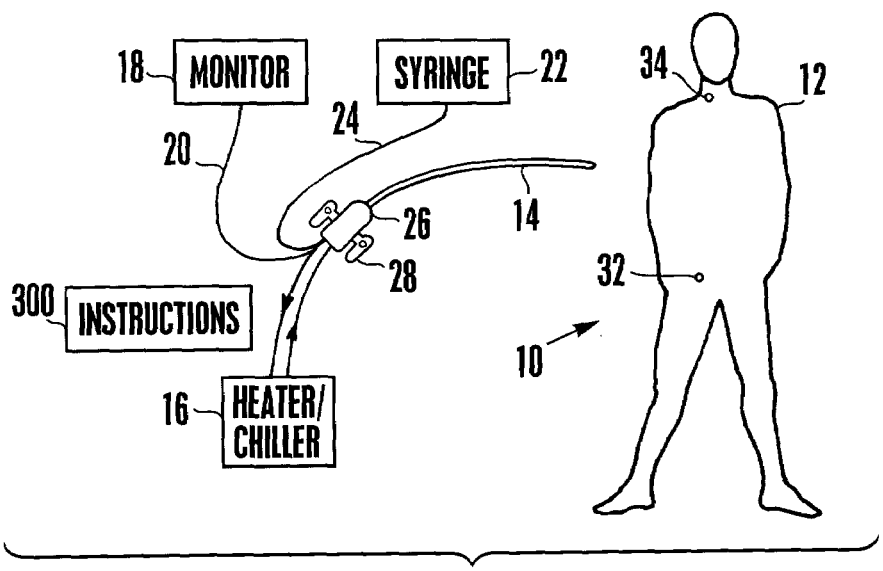
Figure 1
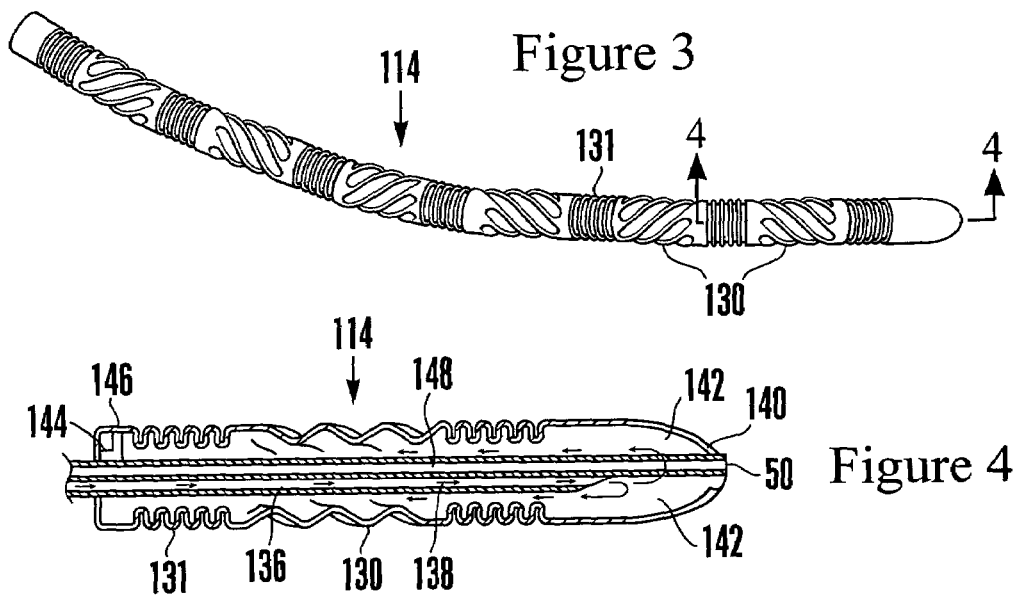
Figure 3
Figure 4
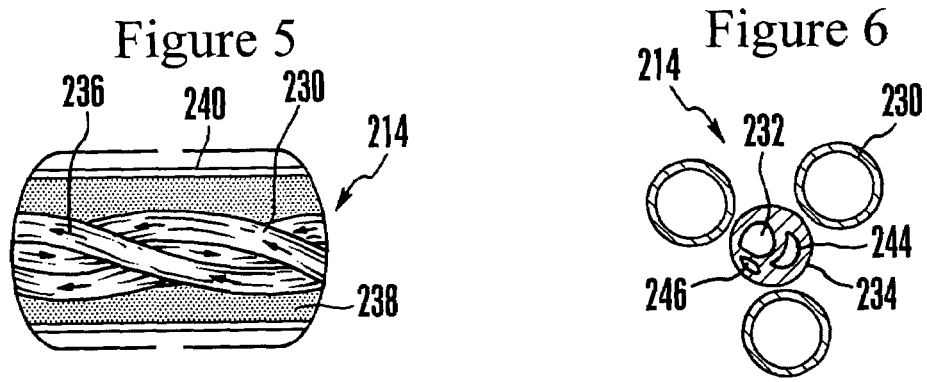
Figure 5
Figure 6

US 7,892,270 B2

TEMPERATURE MANAGEMENT SYSTEM AND METHOD FOR BURN PATIENTS

FIELD OF THE INVENTION

The present invention relates generally to patient temperature control systems.

BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present invention, the above-mentioned advantages in regulating temperature can be realized by cooling or heating the patient's entire body. Moreover, the present invention understands that since many patients already are intubated with central venous catheters for other clinically approved purposes anyway such as drug delivery and blood monitoring, providing a central venous catheter that can also cool or heat the blood requires no additional surgical procedures for those patients. The following U.S. patents, all of which are incorporated herein by reference, disclose various intravascular catheters/systems/methods: U.S. Pat. Nos. 6,749,625, 6,786,916, 6,581,403, 6,454,792, 6,436,130, 6,146,411, 6,109,783, 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,610,083, 6,042,559, and U.S. patent application Ser. No. 10/355,776.

As understood herein the control of body temperature for burn patients is also important, e.g., it would be advantageous to prevent fever in burn patients and/or to prevent eaccidental therapeutic hypothermia in burn patients. For example, heat loss is a common finding in burned victims. Severe hypothermia during operation of debridement of burn wound, especially when patients are sedated and mechanically ventilated, is associated with increased mortality and morbidity. Studies showed almost 100% mortality in severely burned patients who presented with core temperature less than 32° C. The present invention recognizes that current therapeutic approaches such as warm blanket are limited.

SUMMARY OF THE INVENTION

A method includes advancing a closed loop intravascular heat exchange catheter into the vasculature of a burn patient, and establishing a desired patient temperature using the catheter. The catheter may be used to warm the patient during skin graft surgery, as well as to establish normothermia in the patient should the patient become febrile.

In non-limiting implementations the catheter has plural heat exchange elements. In one non-limiting embodiment the heat exchange elements are balloons. In another embodiment the heat exchange elements are metal. In yet another embodiment they are established by plural heat exchange fluid return tubes communicating with a central supply lumen at a distal end of the catheter for carrying heat exchange fluid. In this last embodiment each return tube is formed spirally around the supply lumen such that a body fluid flowing past the return tube exchanges heat with the heat exchange fluid flowing therein.

In another aspect, a system for treating a burn patient includes a heater/chiller and an intravascular catheter configured for receiving working fluid from the heater/chiller and returning working fluid thereto in a closed loop. A substrate is provided bearing instructions for using the catheter to establish a desired patient temperature in the patient.

In yet another aspect, a method for treating a burn patient includes conducting skin graft surgery on the patient, and during surgery, countering hypothermia in the patient using a catheter.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a schematic diagram of a system according to present principles;

FIG. 3 is a perspective view of a second non-limiting catheter;

FIG. 4 is a cross-section as seen along the line 4-4 in FIG. 3;

FIG. 5 is a side view of a portion of a third non-limiting catheter; and

FIG. 6 is a cross-section of the catheter shown in FIG. 5.

DETAILED DESCRIPTION OF THE PREFERRED EMBODIMENT

Figure 2:
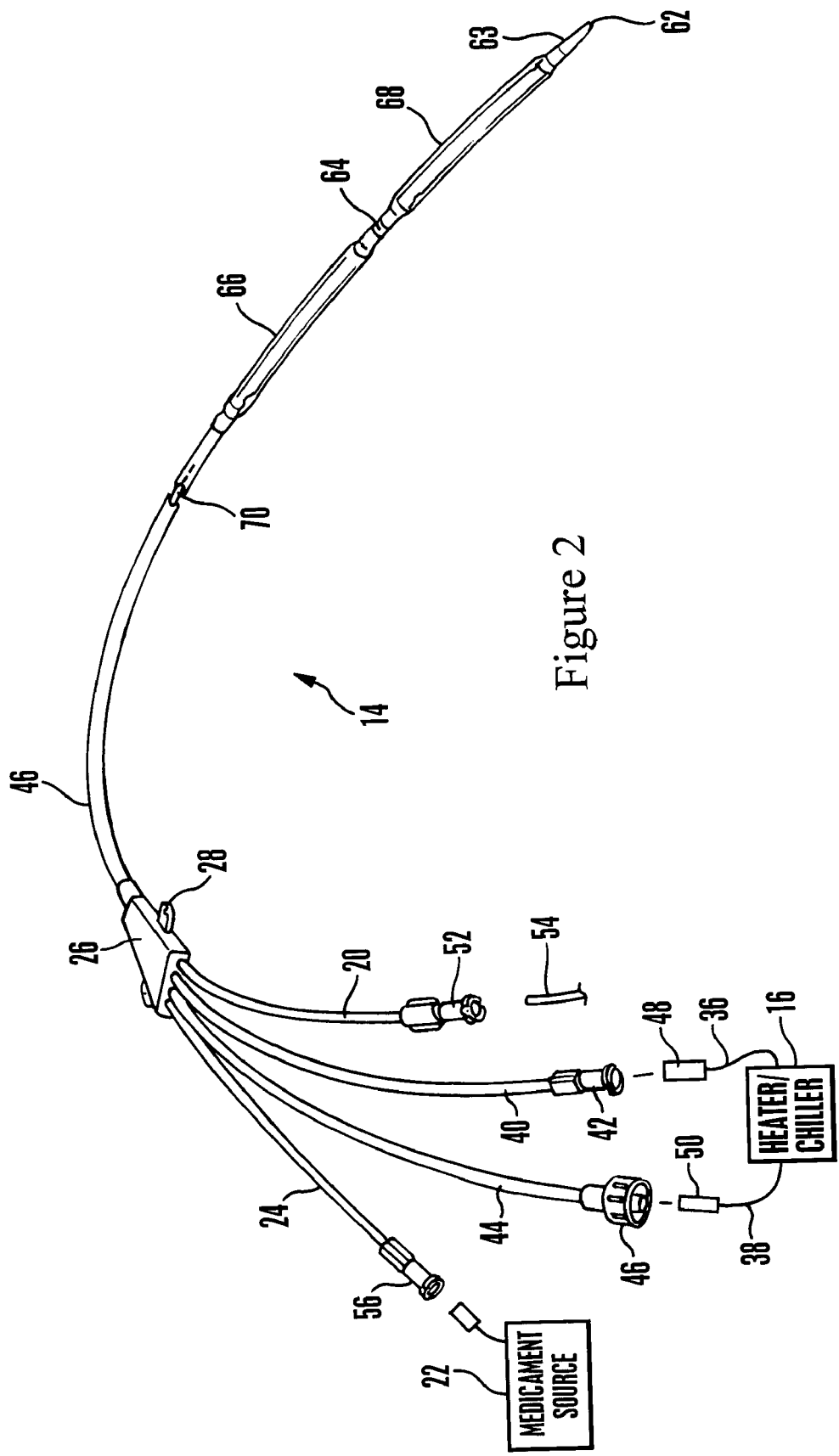
FIG. 2 is a perspective view of a first non-limiting catheter, schematically showing a medicament source and coolant source in an exploded relationship with the catheter.

Referring initially to FIG. 1, a system, generally designated 10, is shown for managing and otherwise controlling whole body temperature of a burn patient 12. The system 10 may be used to establish normothermia in the burn patient 12, i.e., to prevent undesired hypothermia during, e.g., surgery or to prevent hyperthermia in the patient, and/or the system 10 may be used to therapeutically cool the patient 12 to a hypothermic state, e.g., moderate hypothermia around thirty four degrees Celsius. In some implementations discussed below, the system 10 may also be used to provide central venous access to the burn patient 12. In non-limiting implementations the burn patient 12 may be treated with the system upon a predetermined burn threshold, e.g., the body temperature of the burn patient 12 may be managed using the system 10 in the event that the burn patient 12 has suffered third degree burns over thirty percent or more of the patient's body, it being understood that this percentage is not limiting on present principles.

As shown, the system 10 includes an intravascular closed loop heat exchange catheter 14 that receives a heat exchange fluid (also referred to herein as "coolant") from a heater/chiller 16, with the fluid circulating in a closed loop. The fluid can be saline or other fluid such as refrigerant. Either the fluid flow rate and/or the temperature of the fluid is controlled by a controller associated with the heater/chiller 16 based on a patient temperature feedback signal to control the amount and if desired the rate at which heat is added or subtracted from the patient. The controller can be implemented by a software-executing processor or by discrete logic circuits or other electronic circuitry device to establish a desired patient temperature by appropriately controlling the flow rate and/or heat exchanger in response to a temperature signal derived from a sensor in the patient 12. Non-limiting examples of heater/chillers that can be used are disclosed in U.S. Pat. Nos. 7,101,388; 6,878,156; 6,786,916; 6,454,792; 6,454,792; 6,146,411; and 6,019,783, all of which are incorporated herein by reference. Further examples of non-limiting heater/chillers are shown in U.S. Pat. Nos. 6,581,403, 6,436,130, and 6,109,783, incorporated herein by reference.

As also shown in FIG. 1, in some non-limiting implementations at least two central venous (CV) components can be in communication with the catheter 16 for undertaking central venous functions in addition to controlling the temperature of the patient. These functions include and are not limited to drug infusion and blood extraction for blood monitoring, as well as blood pressure monitoring. For instance, a blood monitor 18 can communicate with the catheter 14 via a line 20 to monitor blood pressure or withdraw blood from the central venous system of the patient 12. Also, a syringe 22 can engage the catheter 14 via a connector line 24 for infusing drugs or other medicament such as epinephrine into the patient 12. The components 16, 18, 22 can all be connected to the catheter 14 via a proximal connector hub 26 of the catheter 14. The hub 26 can be formed with a suture anchor 28 or other anchor structure such as tape for providing a means to fasten the catheter 14 to the skin of the patient 14 for long-term use.

The catheter 14 may be any suitable closed loop intravascular temperature control catheter including without limitation in addition to the specific structures disclosed herein, the catheters disclosed in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684.

In any case, once the patient 12 has been diagnosed as suffering skin burns sufficient to warrant management of the temperature of the patient 12, the catheter 12 may be placed in the venous system, e.g., in the superior or inferior vena cava without blocking the vessel so that blood can flow around the catheter to effect heat exchange. In non-limiting embodiments the catheter 14 may be advanced (possibly through an introducer sheath) into the vena cava of the patient 12 through a groin entry point 32 or through a neck entry point 34 to the central venous system of the patient 12. When advanced through the groin the catheter is advanced either through the saphenous vein or femoral vein to the inferior vena cava, and when advanced through the neck through the jugular or subclavian vein to the superior vena cava or inferior vena cava. Less desirably, the catheter 14 may be advanced into the arterial system of the patient 12.

Once disposed in the bloodstream of the patient 12, a target patient temperature is input to the heater/chiller 16. The target temperature can be, e.g., normothermia (i.e., approximately thirty eight degrees Celsius), in which case the heater/chiller 16 controls the temperature and/or flow rate of the coolant circulating through the catheter 14 in response to a patient temperature signal as appropriate to heat or cool the patient to achieve and maintain target temperature. It is to be understood that the patient temperature signal may be generated by a sensor on the catheter 14 and sent to the heater/chiller 16. Or the sensor may be on another device that can be electrically connected to the heater/chiller 16 for sending a patient temperature signal thereto. For example, the sensor may be on a Foley catheter, a rectal temperature probe, an esophageal probe, a tympanic temperature device, or other suitable patient temperature generating device.

Or, target temperature may be below normothermia for the purpose of therapeutically establishing mild or moderate (or even deeper) hypothermia in the patient, in which case the heater/chiller 16 removes heat from the coolant as necessary to achieve and maintain hypothermia for a therapeutic amount of time.

Now referring to FIG. 2 for a description of a first non-limiting catheter 14, commencing at the proximal end the heater/chiller 16 provides coolant such as saline through a coolant supply line 36, and coolant is returned from the catheter 14 via a coolant return line 38. The non-limiting catheter 14 includes a source tube 40 terminating in a fitting such as a female luer fitting 42. Also, the catheter 14 has a return tube 44 terminating in a fitting such a male luer fitting 46. The fittings 42, 46 can be selectively engaged with complementary fittings 48, 50 of the lines 36, 38 to establish a closed circuit coolant path between the catheter 14 and heater/chiller 16.

Additionally, the non-limiting catheter 14 shown in FIG. 2 may include the primary infusion tube 20 as mentioned above that can also be used as a guidewire tube. The tube 20 terminates in a fitting such as a female luer 52. A guide wire 54 or the syringe 22 shown in FIG. 1 can be advanced through the tube 20 in accordance with central venous catheter placement principles, or the monitor 18 shown in FIG. 1 may be engaged with the tube 20.

Moreover, the connector line 24, which can establish a secondary infusion tube, can end in a female luer fitting 56 that can be selectively engaged with, e.g., the syringe 22 for infusing fluid from the syringe or other source such as an IV bag into the patient.

The tubes 20, 24, 40, 44 are held in the hub 26, which may be distally tapered as shown. As set forth in U.S. Pat. No. 6,368,304, incorporated herein by reference, the hub 26 establishes respective pathways for fluid communication between the tubes 20, 24, 40, 44 and respective lumens in the body 46 of the catheter 14. The suture anchor 28 advantageously may be formed on the hub 26 for suturing the catheter 14 to a patient in accordance with central venous catheter operating principles.

The non-limiting the catheter body 46 may include at least two lumens, and in a preferred embodiment the catheter body 46 includes at least four lumens and more preferably has five lumens. Two of the lumens are coolant supply and return lumens through which coolant is circulated to and from one more distally-located, axially-spaced thin-walled heat exchange membranes 66, 68 (two shown) that are arranged along the last fifteen or so centimeters of the catheter body 46 and are bonded to the outer surface of the catheter body 46, with an infusion port 64 being located between the heat exchange membranes 66, 68. Essentially, the heat exchange membranes 66, 68 extend along most or all of that portion of the catheter 46 that is intubated within the patient. The heat exchange membranes can be established by a medical balloon material. When coolant is circulated through them the heat exchange membranes may define a diameter of about ten French, and preferably no more than twelve French in non-limiting embodiments. Thus, the heat exchange membranes 66, 68 are relatively long and comparatively thin, to advantageously avoid excessively blocking blood flow through the vena cava while nevertheless effecting patient cooling. If desired, a temperature sensor 70 such as a thermistor or other suitable device can be attached to the catheter 14 as shown by solvent bonding at a point that is proximal to the membranes 66, 68. The sensor 70 provides patient temperature feedback to the heater/chiller 16 through a wire disposed in the catheter 14. Or, the sensor 70 can be disposed in a lumen of the catheter 14, or attached to a wire that is disposed in a lumen of the catheter 14, with the sensor hanging outside the catheter 14. Alternatively, a separate temperature probe can be used, such as an esophageal probe, a rectal probe or tympanic temperature sensor.

FIGS. 3 and 4 show another non-limiting intravascular closed loop heat exchange catheter that can be used, generally designated 114. As shown in FIG. 3, the catheter 114 can include plural heat exchange elements 130. The heat exchange elements 130 can be established by one or more metal, preferably gold, hollow elongated segments that have external surfaces which have turbulence-inducing irregular exterior surfaces that are shaped to induce gentle turbulence in blood flowing past the elements. Separating adjacent heat exchange elements 130 can be a flexible articulating joint 131, it being understood that the heat exchange elements 130 and joints 131 can be formed from a single piece of material such as plastic or metal, e.g., gold. The details of the heat exchange elements 130 and their configuration are set forth in U.S. Pat. Nos. 6,554,797 and 6,096,068, incorporated herein by reference. In any case, coolant is circulated in a closed fluid communication loop between the heat exchange elements 130 and heater/chiller 16 to remove heat from the patient 12 or to add heat to the patient to rewarm the patient.

Now referring to FIG. 4, it can be seen that in non-limiting implementations the catheter 114 if desired may establish a tubular conduit that is disposed substantially coaxially within the heat exchange elements 130, with the conduit having a supply lumen 136 for supplying a pressurized working fluid (represented by arrows 138) to a distal end 140 of the catheter 114. As the fluid exits the supply lumen 138, it flows out and around the supply lumen 138 in a proximal direction as shown in an annular return lumen 142. It may readily be appreciated that heat is exchanged between the fluid 138 and bloodstream into which the catheter 114 is placed across the walls of the heat exchange elements 130 to heat or cool the patient as desired.

In addition to the supply and return lumens 136, 142, the catheter 114 if desired may have at least two and possibly more infusion or working lumens (only two shown for clarity) for undertaking CV functions simultaneously with controlling patient temperature. Specifically, as shown in FIG. 4, a first infusion or working lumen 144 terminates in a first outlet port 146, and a second infusion or working lumen 148 terminates in a second outlet port 150. Both lumens 144, 148 are separated from the fluid 138 and both lumens 144, 148 preferably extend to the hub 26 shown in FIG. 1. The second infusion or working lumen 148 can be coaxial with the body of the catheter 114 as shown. The second port 150 can be located on the distal tip of the catheter 114 as shown. In any case, to provide for mixing of infused drugs in the bloodstream if two drugs are to be administered, the ports 146, 150 are longitudinally separated from each other as shown. With the above in mind, the monitor 18 (FIG. 1) or other CV device such as an infusion device can communicate with one of the infusion or working lumens 144, 148 while the syringe 22 can communicate with the other infusion or working lumen 148, 144.

As an alternative to the catheters 14, 114, a catheter 214 shown in FIGS. 5 and 6 and disclosed in U.S. Pat. Nos. 6,585,692 and 6,610,083, both of which are incorporated herein by reference, may be used. The catheter 214 can include plural heat exchange elements 230. The heat exchange elements 230 can be established by, e.g., three coolant return tubes made of hollow plastic, with each tube establishing a respective coolant return lumen. As shown best in FIG. 6, a central coolant supply lumen 232 that is established by a center tube 234 is also provided. It is to be understood that the supply lumen 232 conveys coolant from the heater/chiller 16 in a distal direction along the catheter 214, whereas the heat exchange elements 230 (the coolant return tubes) convey coolant back to the heater/chiller 216 in a proximal direction as indicated by the arrows 236 in FIG. 5. With this structure, blood 238 in a central venous system vein 240 into which the catheter 214 is advanced is cooled (or heated) by exchanging heat with the coolant across the walls of the heat exchange elements 230. Thus, coolant is circulated in a closed fluid communication loop between the heat exchange elements 230 and heater/chiller 16 to remove heat from the patient or to add heat to the patient to rewarm the patient after surgery or after the termination of therapeutic hypothermia treatment.

The coolant return tubes are spirally formed around the center tube 234, and can be adhered thereto or not. That is, non-limiting heat exchange elements 230 define spirals. The length "L" of the heat exchange region of the catheter 214 can be about 250 millimeters, with the pitch of the spiral heat exchange elements 230 being about 64 millimeters. In any case, the coolant supply lumen 232 terminates in a hollow distal tip, as do the lumens of the heat exchange elements 230. Accordingly, coolant passes from the supply tube to the return tubes at the distal tip.

Additionally, as best shown in FIG. 6, the center tube 234 can establish one or more working lumens (only two shown in FIG. 6 for clarity of disclosure) for undertaking CV functions simultaneously with controlling patient temperature. In the embodiment shown, the center tube 234 establishes first and second working lumens 244, 246 that have any suitable cross-sectional shape and that can respectively communicate with the central venous components 18, 22 discussed above. Both working lumens 244, 246 are separated from the coolant and both working lumens preferably extend to the hub 26 shown in FIG. 1. The working lumens 244, 246 can terminate in respective exit ports that may be longitudinally spaced from each other, e.g., one port can be at the distal tip of the catheter 214 and the other port can be located somewhat proximal to the tip.

Any of the catheters disclosed herein can be used to maintain normothermia in the burn patient 12, typically by warming the patient. For example, the catheters 14, 114, 214 can be used during surgery to keep patient temperature above 36 C when replacing necrotic skin with grafts. Without the present invention, it is often the case that patient temperature drops so that only one limb at a time may be repaired with grafts, but with the present invention grafts on all limbs may be completed during the same surgery.

Temperature management of the patient 12 may be maintained after surgery using the system 10 for, e.g., thirty days, with a catheter change every few days if desired, with the patient in the burn unit and/or hospital ICU.

In one non-limiting treatment protocol, the patient is older than 18 years and presents with a core temperature of under 37° C. Target temperature can be set to 36.5° C. and warming rate to maximum. A core temperature monitor is established by, e.g., placing an esophageal/Foley/rectal temperature probe in the patient, with the monitor connected to the heater/chiller 16. Warming is commenced as early as possible to prevent core temperature drop. The catheter 14 can also be used as a multi-lumen central venous catheter to deliver warm fluid such as saline, medications, to withdraw blood or conduct other monitoring acts of patient parameters. All of these steps can take place during and after skin graft surgery. Subsequently, should the patient develop fever, the catheters 14, 114, 214 can also be used to control hyperthermia. A substrate 300 (FIG. 1) may be provided that bears instructions for using the present catheter to establish a desired patient temperature in the burn patient 12 in accordance with principles set forth herein.

While the particular TEMPERATURE MANAGEMENT SYSTEM AND METHOD FOR BURN PATIENTS is herein shown and described in detail, it is to be understood that the subject matter which is encompassed by the present invention is limited only by the claims.

What is claimed is:

1. A method comprising:
   advancing a closed loop intravascular heat exchange catheter into the vasculature of a burn patient; and
   establishing a desired patient temperature using the catheter, wherein the catheter has plural heat exchange elements, wherein the heat exchange elements are established by plural heat exchange fluid return tubes communicating with a central supply lumen at a distal end of the catheter for carrying heat exchange fluid, each return tube being formed spirally around the supply lumen such that a body fluid flowing past the return tube exchanges heat with the heat exchange fluid flowing therein.

2. The method of claim 1, wherein the catheter is used to warm the patient during skin graft surgery.

3. The method of claim 2, wherein the catheter is used to establish normothermia in the patient should the patient become febrile.

4. The method of claim 1, wherein the heat exchange elements are balloons.

5. The method of claim 1, wherein the heat exchange elements are metal.

6. A method for treating a burn patient comprising:
   conducting skin graft surgery on the patient; and
   during surgery, countering hypothermia in the patient using a catheter.

7. The method of claim 6, wherein the catheter is used to establish normothermia in the patient should the patient become febrile.

8. The method of claim 6, wherein the catheter has plural heat exchange elements.

9. The method of claim 8, wherein the heat exchange elements are balloons or are metal.

10. The method of claim 6, comprising using the catheter to undertake at least one central venous line function selected from the group consisting of: infusing medicament into the bloodstream, infusing saline into the bloodstream, and monitoring a patient parameter.

11. The method of claim 10, wherein the act of countering hypothermia is executed by circulating working fluid through the catheter such that the working fluid does not enter the bloodstream and exchanges heat therewith.

* * * * *